(12) United States Patent
Daniel (10) Patent No.: US 9,053,625 B2
(45) Date of Patent: Jun. 9, 2015

(54) SYSTEM AND METHOD FOR GROUP TRACKING

(75) Inventor: Isaac Sayo Daniel, Miami, FL (US)

(73) Assignee: The F3M3 Companies, Inc.

(*) Notice: Subject to any disclaimer, the term of this patent is extended or adjusted under 35 U.S.C. 154(b) by 604 days.

(21) Appl. No.: 12/315,547

(22) Filed: Dec. 4, 2008

(65) Prior Publication Data

US 2010/0141393 A1    Jun. 10, 2010

(51) Int. Cl.
| | |
|---|---|
| *G08B 13/14* | (2006.01) |
| *G08B 23/00* | (2006.01) |
| *G08B 21/00* | (2006.01) |
| *G08B 1/08* | (2006.01) |
| *H04W 24/00* | (2009.01) |
| *H04B 7/00* | (2006.01) |
| *G01S 19/42* | (2010.01) |
| *G08B 21/02* | (2006.01) |
| *A43B 3/00* | (2006.01) |
| *G06Q 10/08* | (2012.01) |
| *G07C 9/00* | (2006.01) |
| *H04W 4/02* | (2009.01) |
| *H04L 29/08* | (2006.01) |
| *A61B 5/11* | (2006.01) |

(52) U.S. Cl.
CPC .............. *G08B 21/0283* (2013.01); *A43B 3/00* (2013.01); *A61B 5/1112* (2013.01); *G06Q 10/08* (2013.01); *G07C 9/00103* (2013.01); *G07C 9/00111* (2013.01); *G08B 21/0227* (2013.01); *G08B 21/0269* (2013.01); *H04Q 2213/13003* (2013.01); *H04W 4/02* (2013.01); *H04L 67/125* (2013.01); *H04L 67/04* (2013.01); *H04L 67/18* (2013.01)

(58) Field of Classification Search
USPC ....................................................... 340/10.3
See application file for complete search history.

(56) References Cited

U.S. PATENT DOCUMENTS

| | | | | |
|---|---|---|---|---|
| 6,278,370 | B1 * | 8/2001 | Underwood | 340/573.1 |
| 6,975,873 | B1 * | 12/2005 | Banks et al. | 455/456.5 |
| 2007/0229350 | A1 * | 10/2007 | Scalisi et al. | 342/350 |

* cited by examiner

*Primary Examiner* — Brent Swarthout
*Assistant Examiner* — John Mortell
(74) *Attorney, Agent, or Firm* — Carol N. Green Kaul, Esq.

(57) ABSTRACT

The present invention relates generally to a system and method for group tracking wherein at least one individual within a tracked group is provided with an article of footwear equipped with a wireless tracking device. The wireless tracking device is configured for bi-directional communications with a monitoring center, wherein the wireless tracking device is adapted to determine and store absolute location information of the individual wearing the wireless tracking device and the location information of at least one other individual within the tracked group. Each individual's tracking device has a unique identifier for identifying the individual with a monitoring center at a remote location and/or portable monitoring unit.

16 Claims, 7 Drawing Sheets

SYSTEM AND METHOD FOR GROUP TRACKING

FIELD OF THE INVENTION

The present invention relates generally to a system and method for group tracking using an advanced communication system network for tracking and monitoring each individual in a group wherein each individual is provided with an article of footwear having a tracking device that can be selectively engaged by the individual to transmit an encoded signal containing the individual and/or the group's specific location to a monitoring center.

DESCRIPTION OF THE PRIOR ART

Mountain climbers, hikers, guided tours, boy scouts and military troops often travel outdoors to remote locations navigating unpredictable, difficult terrain in primitive surroundings with relatively little distance between each group member. Generally, the communications are organized with a centralized control, where the majority of the communications take place between the group leader and individual group members. External communications are similarly directed to, and through the group leader where only occasionally individual group members communicate directly with each other and/or the external world.

Emergencies often alter those communications dynamics as individual group members may need to transmit or receive external communications. Thus, it is no surprise that rescue parties often lose precious time locating individuals and/or the group because generally there is no readily implementable system and method for dynamically tracking the group and/or its individual members as they travel over remote terrain. In those circumstances, use of public wireless networks is often impossible or impractical because of nonexistent electrical or wireless service or there is limited access to necessary resources, e.g. power supply, to effectuate the communication. Satellite phones offer a limited solution as the cost of satellite service prohibits widespread general use. Thus, it would be useful to be able to track a group's movements both collectively and individually as they travel in remote locations to determine for example, their location at any given point in time. It would also be useful for the group to be able to provide information to the external world as to the group's and/or its individual member's geographical location at any given time.

The prior art suggests that Global Positioning Systems ("GPS") may offer a limited solution as it is widely used for other like applications, for e.g. (i) personal tracking systems where it records and reports individual's geographical position and/or the distance travelled from a fixed location; (ii) vehicle and personal navigational systems by providing maps and directions from a current location to the destination as well as reporting geographical position and other pertinent information, e.g. average speed travelled over the distance; (iii) geo-fencing by controlling the movement of an individual or a valuable asset from straying or being removed beyond a predefined area; and (iv) asset management systems which provide current geographical position of valuable movable assets.

The afore-mentioned groups usually travel from a common starting point to a common destination. Therefore, effective tracking of these groups will require elements of navigation assistance, particularly for the group leader, as well as elements of geo-fencing where the "geo-fence" may be determined as the maximum allowable distance away from the group leader or the majority of the group members ("center of gravity"). However, unlike typical geo-fencing systems of the prior art, here the "geo-fence" is in constant motion. Likewise, applying strict asset management systems technology of the prior art would be ineffective as here, group tracking transactions comprise of bi-directional communications, which may be initiated either by the monitoring center, individual group members and/or by the group leader. Thus, there exists a need to be able to track the location of a group collectively and/or individually where both the group leader and/or its members are in constant motion and are constantly changing directions. Similarly, there exists a need to facilitate bi-directional communications for mobile individuals traveling in a group in remote locations.

This invention satisfies these long felt needs in a new and novel manner and solves the foregoing problems that the prior art has been unable to resolve.

SUMMARY OF THE PRESENT INVENTION

The present invention relates generally to a system and method for group tracking wherein at least one individual within a tracked group is provided with an article of footwear equipped with a wireless tracking device. The wireless tracking device is configured for bi-directional communications with a monitoring center, wherein said wireless tracking device is adapted to determine and store absolute location information of the individual wearing the wireless tracking device and the location information of at least one other individual within the tracked group. The location information may comprise of but is not limited to: an individual's absolute geographical location, the date and time the location information was determined and/or the individual's location relative to other individuals within the tracked group. Each individual's tracking device has a unique identifier for identifying said individual with a monitoring center at a remote location and/or portable monitoring unit.

The wireless tracking device also includes communications means for receiving an activation signal emitted from a monitoring center and/or the communications means of another wireless tracking device worn by an individual within the tracked group. The wireless tracking device is provided with a microcontroller, which includes determining means for determining said wireless tracking device's direct access to a satellite network system. If the wireless tracking device has direct access to a satellite network system, upon activation the individual's location information may be determined and transmitted to a portable monitoring unit or a monitoring center at a remote location via a satellite network system. The satellite network system may include one of the following: a geosynchronous or low earth orbit satellite.

If the wireless tracking device does not have direct access to a satellite system, the wireless tracking device's microcontroller dynamically creates a relay path of transmission to the satellite network system by querying nearby wireless tracking devices within the tracked group until at least one wireless tracking device with direct access to the satellite network system is determined. The wireless tracking device's communications means then transmit an encrypted signal containing location information of at least one individual within said tracked group along the dynamically created relay path of transmission, where the individual's location information is received and stored for transmission along the dynamically created relay path to the monitoring center at a remote location via said satellite network system.

Accordingly, each individual group member's location information may be transmitted and stored for transmission to the portable monitoring unit and/or monitoring center even though an individual's wireless tracking device may lack direct access to a satellite network system. The location information being transmitted to the monitoring center may therefore include any one or more of the following but is not limited to: the absolute geographical location for one, some or all individuals wearing the wireless tracking device in the tracked group.

The communication means for transmitting and receiving encrypted signal may comprise of a short range wireless protocol which includes a combined wireless transceiver with integrated radio and shared antennae, which may include any one or more of the following in combination, e.g. WiHLoN™, ZigBee, Bluetooth®, 802.11 series, or any other short range wireless protocol that is well known and used in the arts. Preferably, the communication means and the microcontroller's encrypting/decrypting means include a combined wireless transceiver like a ZigBee transceiver with an integrated radio and shared antennae.

A primary object of the present invention is to provide a system and method for group tracking that overcomes the limitations of the prior art.

Another object of the present invention is to provide real-time location information for individuals within a tracked group as they travel over remote locations.

Still another object of the present invention is to provide a system and method wherein a monitoring center is able to identify and monitor the movements and/or activities of a group and or its individual members.

Yet another object of the present invention is to provide a system and method for tracking a group using bi-directional communications transactions to determine the group and/or its individual's location at any given point in time during a tracking session, i.e. a problem which the prior art has not been able to solve.

An even further object of the present invention is to provide a system and method for group tracking using an article of footwear equipped with a wireless tracking device, wherein the footwear is at least one of a men's shoe and a women's shoe.

Still another object of the present invention is to provide a system and method for group tracking using an article of footwear, wherein the footwear is at least one of a sneaker, a casual shoe, a loafer and a dress shoe.

Another objective of the invention is to readily identify the identity and location of an individual within a group that is being tracked.

Another objective of the invention is to provide a system and method for monitoring all individuals in a group in an expedient and efficient manner.

For a further and more fully detailed understanding of the present invention, various objects and advantages thereof, reference is made to the following detailed description and the accompanying drawings.

The foregoing and other objects and advantages will appear from the description to follow. In the description, references are made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

Further objectives and advantages of the present invention may be derived by referring to the detailed description and claims when considered in connection with the Figures, wherein like reference numbers refer to similar items throughout the Figures.

DETAILED DESCRIPTION OF THE PREFERRED EMBODIMENT

The following discussion describes in detail one embodiment of the wireless tracking device and the system and various methods of tracking a group and its individual members. However, this discussion should not be construed as limiting the invention to those particular embodiments as practitioners skilled in the art will recognize numerous other embodiments as well. For definition of the complete scope of the invention, the reader is directed to appended claims. Turning now descriptively to the drawings, in which similar reference characters denote similar elements throughout the several views.

Figure 1A:
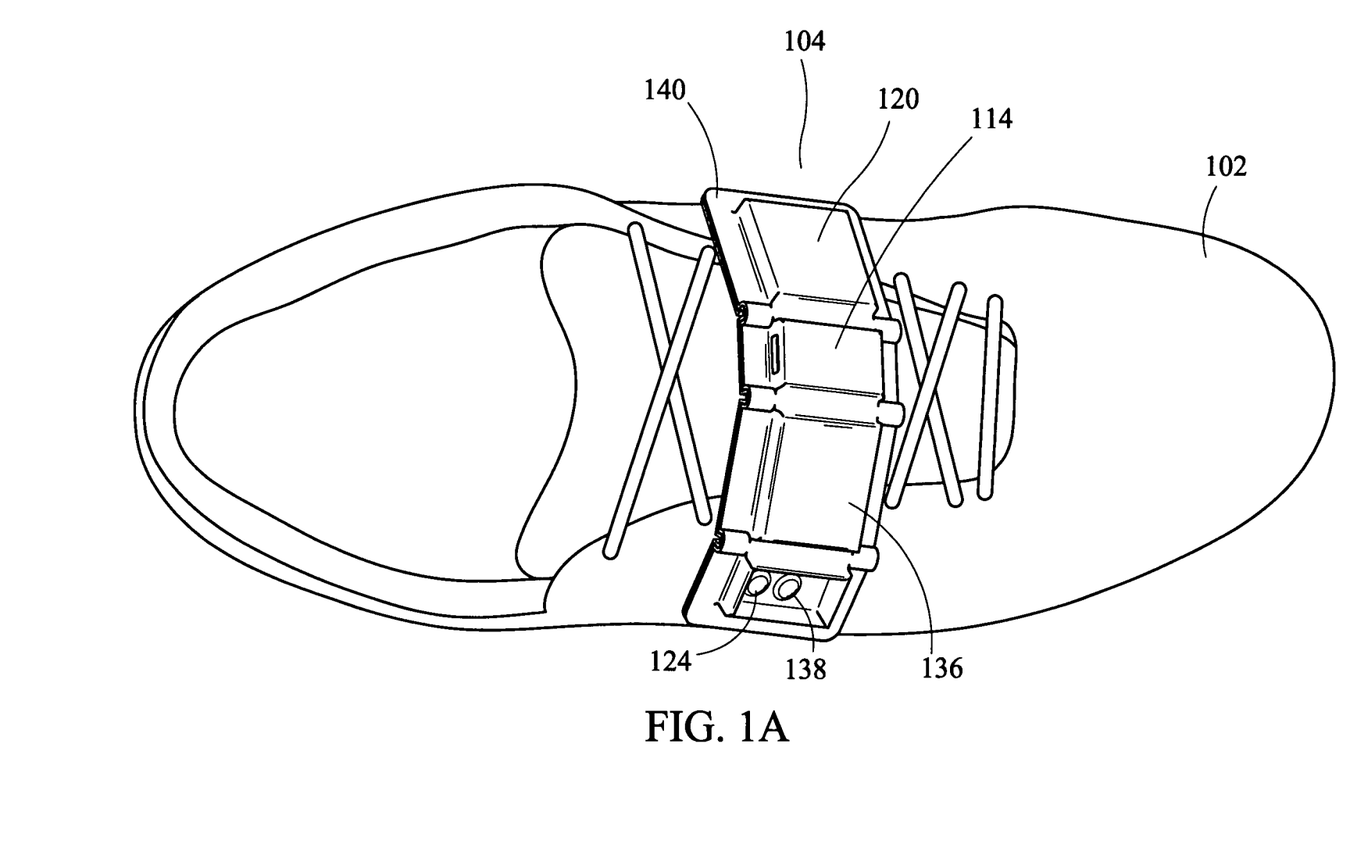
FIG. 1A is an illustrative view of a wireless tracking device of the present invention.
Figure 1B:
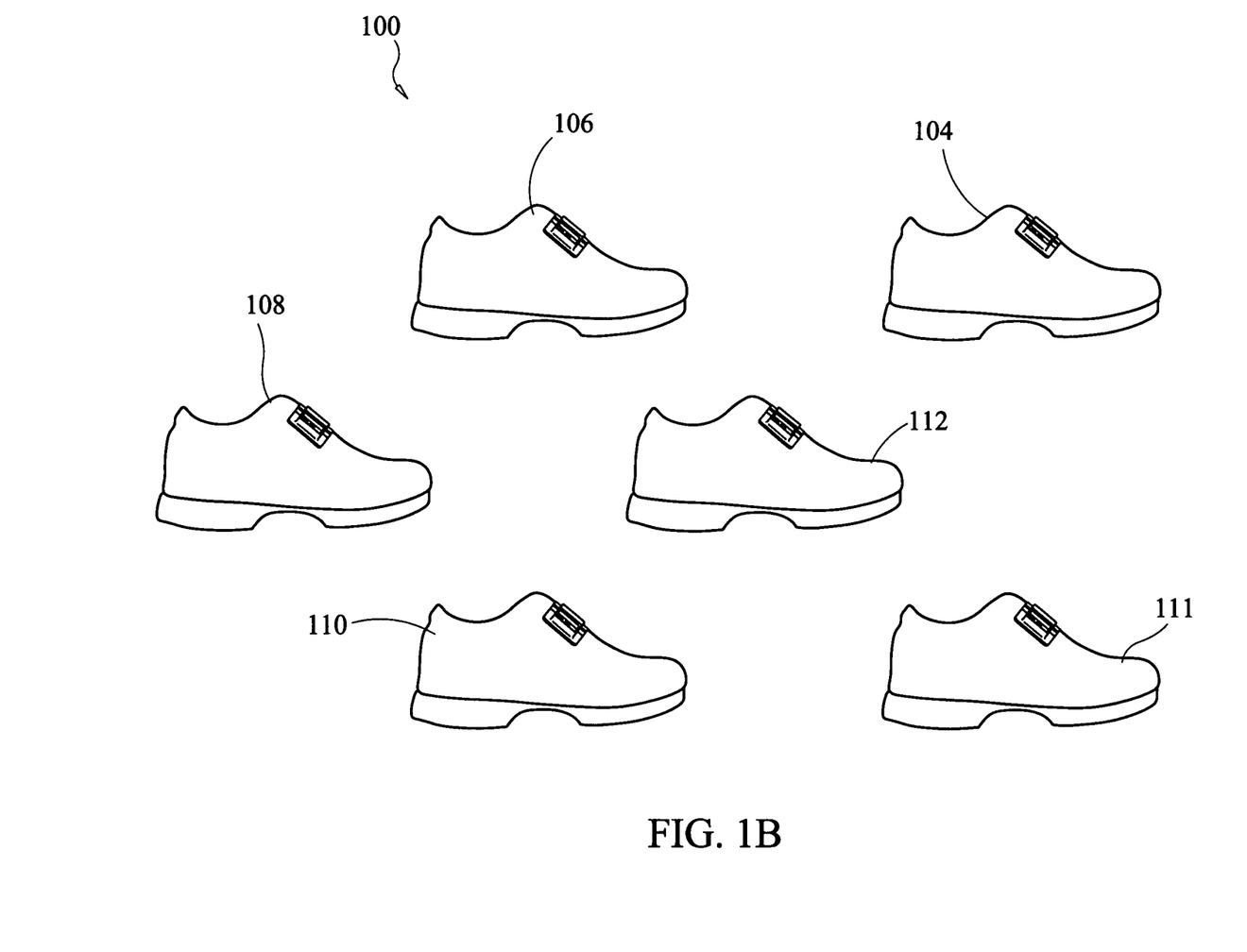
FIG. 1B is an illustrative view of a plurality of wireless tracking devices in accordance with an embodiment of the invention.

FIG. 1A is an illustrative view of a wireless tracking device 104 in accordance with an embodiment of the present invention. The present invention is a system 100 and methods for tracking groups by providing at least one individual within a tracked group with an article of footwear 102. As shown herein, the footwear 102 is a sneaker. However, footwear 102 may be any type and style of men's and/or women's footwear 102. Referring to FIG. 1B, each article of footwear 102 is equipped with a wireless tracking device 104, 106, 108, 110, 111, 112, which is shown for illustrative purposes only, as there may be more or less wireless tracking devices within the tracked group. Here, wireless tracking devices 104, 106, 108, 110, 111, 112 are located on the upper portion of the footwear 102. This is shown for illustrative purposes only, as wireless tracking devices 104, 106, 108, 110, 111, 112 may be positioned along any portion of the exterior surface of the footwear 102.

Referring back to FIG. 1A, each wireless tracking devices 104 is equipped with communication means 114 for the receipt and transmissions of wireless communications through a wireless communications network system 116 (not shown), which is preferably a satellite network system 118. Said communication means 114 may include any one or more of the following short range wireless protocol, WiHLoN™, ZigBee, Bluetooth®, 802.11 series, or any other short range wireless protocol that is well known and used in the art and other future short range wireless protocol suitable for transmitting and receiving data over a short distance. Preferably, communication means 114 comprises of a combined wireless transceiver with integrated radio and shared antennae, e.g. WiHLoN™, ZigBee, Bluetooth®, 802.11 series, or any other short range wireless protocol that is well known and used in the art, in mating engagement with an autonomous power supply 120, e.g. a rechargeable battery.

Said communication means 114 may transmit at least one encrypted signal containing the individual's location information to a monitoring center 122, and/or a neighboring wireless tracking device 104. The location information may comprise of the individual's absolute geographical location, the date and time the location information was determined and/or the individual's location relative to other individuals within the tracked group. Wireless tracking device 104 has a unique identifier to identify and register an individual with a monitoring center 122.

Wireless tracking device 104 includes an activation button 124, which may be selectively depressed to either activate and/or deactivate transmission of the individual's location information to monitoring center 122. The activation button 124 may be covered by a switch cover 126 (not shown) that is hingedly connected to the exterior side of the footwear 102 by a hinge 128 (not shown). Preferably, the switch cover 126 (not shown) is semi-rigid in order to prevent accidental activation. As shown in FIG. 1, the activation button 124 is positioned at the top portion of the footwear 102. This is shown for illustrative purposes only, as activation button 124 may be positioned along any portion of footwear 102.

Wireless tracking device 104 also includes alarm notification means 130 (not shown) which may comprise of a speaker 132 (not shown) capable of sounding an audio alarm; a single tone alert system 134 (not shown) sounding an alarm like Sonalert; or a microcontroller 136 electrically connected to an alarm button 138 programmed to flash a light thereon on receipt of an encrypted alarm signal from monitoring center 122.

Each wireless tracking device 104 includes a circuit board 140 having an autonomous power supply 120, a microcontroller 136 and communication means 114 positioned thereon, interconnected by an electrical network 142 (not shown) by conventional electrical elements as is well known and used in the art. Conventional wires connect the circuit board 140 with microcontroller 136, activation button 124, and the alarm button 138. The circuit board 140 may be formed from silicon, fiberglass, Kapton®, Mylar, or other suitable materials that remain stable in a wide range of extreme temperatures that are well known and used in the art. An antenna 144 (not shown) is electrically connected to microcontroller 136 on the circuit board 140 or alternatively imbedded within microcontroller 136.

Figure 2:
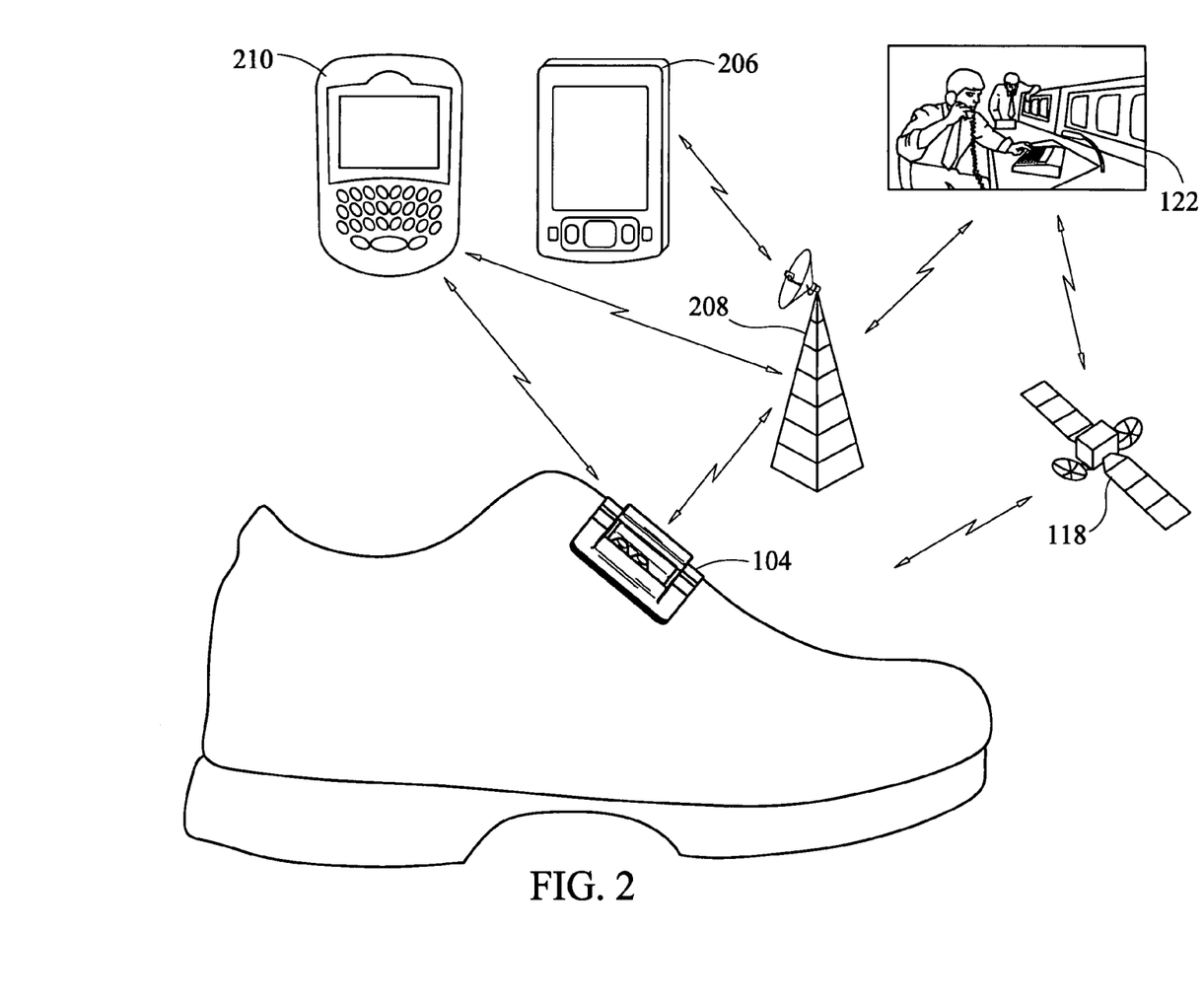
FIG. 2 is an illustrative view of a system of tracking individuals according to an embodiment of the present invention.
Figure 3:
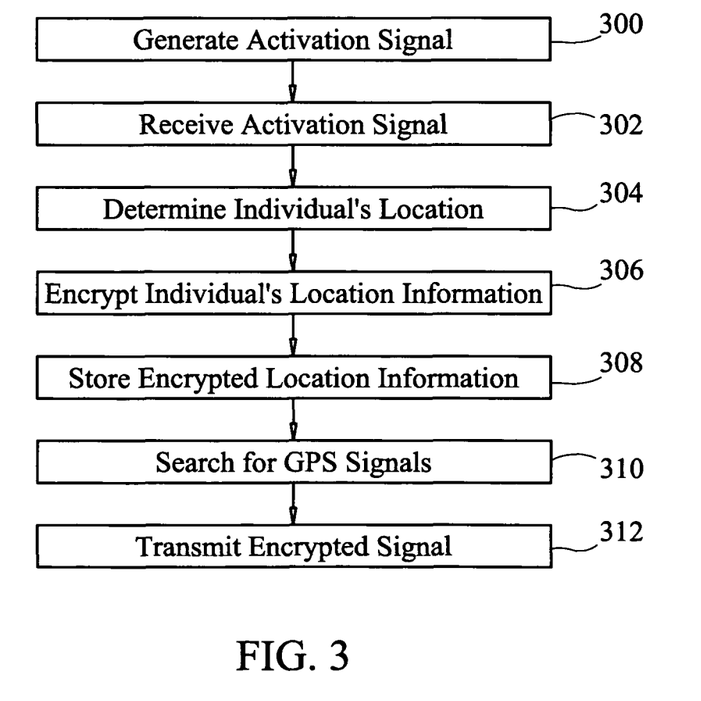
FIG. 3 shows an illustrative flowchart of a method of tracking individuals according to an embodiment of the present invention.
Figure 4:
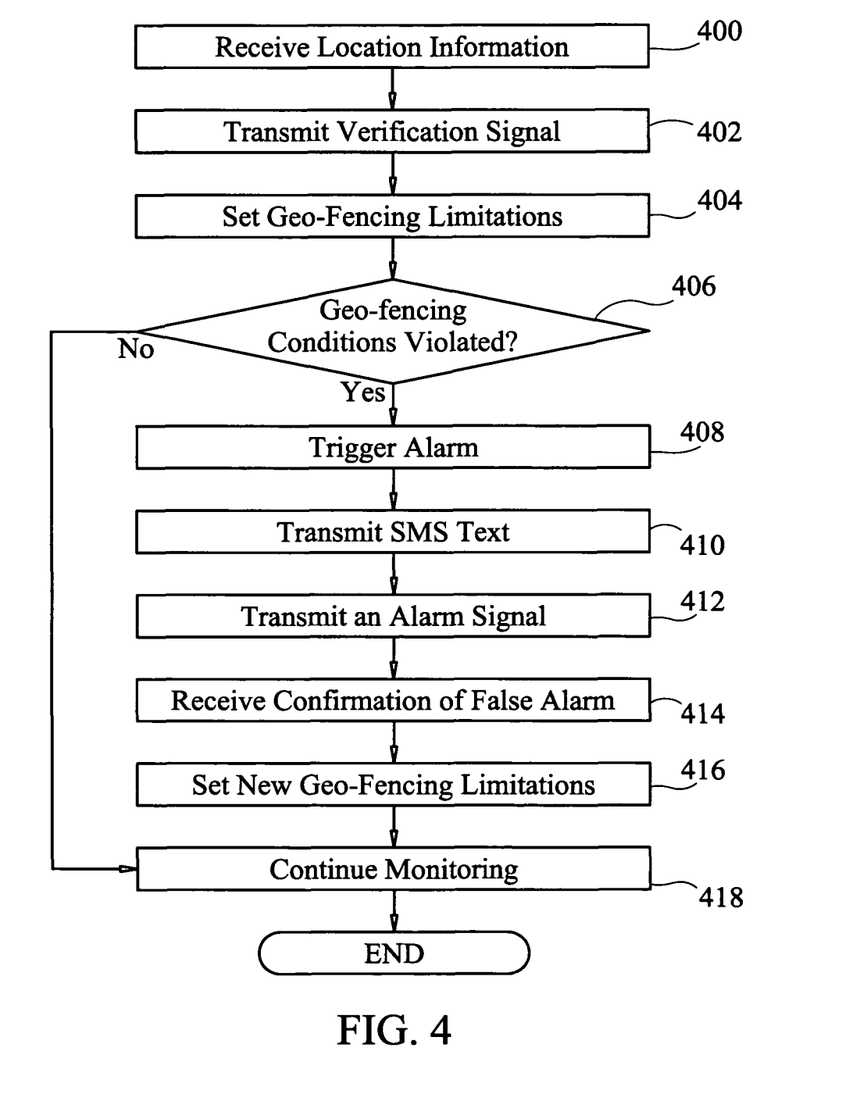
FIG. 4 shows an illustrative flowchart of a method of tracking individuals according to an embodiment of the present invention.

FIGS. 2, 3 & 4 show an illustrative view of a system 100 of tracking individuals according to an embodiment of the present invention and illustrative flowcharts of methods, of tracking individuals according to embodiments of the present invention.

Referring to FIG. 3, upon activation, microcontroller 136 of wireless tracking device 104 causes an activation signal to be generated (step 300). Communication means 114 receives the activation signal in step 302. Communication means 114 is configured to receive at least one encrypted alarm signal from a monitoring center 122 and/or an encrypted signal containing an individual's location information from a neighboring wireless tracking device 104 within the tracked group.

Each wireless tracking device's 104 microcontroller 136 includes determining means 200 (not shown), e.g. a GPS transponder 202 (not shown), which upon activation, orients itself and determines the individual's location information in step 304. Microcontroller 136 creates an encrypted signal (step 306) containing the individual's location information, which is stored in the wireless tracking device's 104 memory means 211 (step 308). Memory means 211 may include one of, or a combination of, but is not limited to RAM, SRAM, DRAM storage media or any other form of recording and storage media that are well known and used in the arts suitable for practicing the invention.

Determining means 200 (not shown) searches for signals of GPS satellite constellation 204 (not shown) (step 310), verifying whether wireless tracking device 104 has direct access to a satellite network system 118. In FIG. 2, an exemplary wireless tracking device 104 has direct access. If so, communication means 114 transmits the encrypted signal (step 312) directly to the satellite network system 118, which re-transmits the encrypted signal to the monitoring center 122. In one embodiment of the present invention, communication means 114 may communicate with monitoring center 122 via either a geosynchronous (GEO) or Low Earth Orbit (LEO) satellite in a network.

Referring to FIGS. 2 and 4, tracking may occur at a stationary, brick and mortar site or wirelessly via a portable monitoring unit 206. Communications between the individuals being tracked and monitoring center 122 and/or portable monitoring unit 206 (collectively "monitoring center 122") are bi-directional, wherein monitoring center 122 may also communicate with, for example, a designated group leader and/or other individuals within the tracked group. When wireless tracking device 104 is activated, monitoring center 122 receives the location information (step 400) from each activated wireless tracking device 104 and verifies each individual's location by transmitting a verification signal (step 402) to each wireless tracking device 104 via either a GSM communications network 208, or to a satellite network system 118, which retransmits the signal to the individual wireless tracking devices 104, 106, 108, 110, 111, 112. Each wireless tracking device 104 acts as nodes and/or routers wherein radio communications flow from one wireless tracking device 104 to another. In this manner, the range of radio communications is only limited to the distance between any two of the nearby wireless tracking devices 104, 106, 108, 110, 111, 112, allowing the group as a whole to be dispersed over a radius of several miles.

Monitoring center 122 sets geo-fencing limitations for the group's individuals (step 404) in real-time based on the group's center of gravity as they travel. The "geo-fence" may be defined as the maximum allowed distance to the group leader or to the majority ('center of gravity") of the group members, where the "geo-fence" is in constant motion. Monitoring center 122 confirms whether geo-fencing conditions have been violated (step 406) by any individuals within the group by determining each individual's location relative to the predefined geo-fencing limitations, i.e. relative distance between individual members of the group, to confirm that individuals are still within predefined geo-fencing limitations. If during a tracking session, no geo-fencing conditions have been violated, monitoring center 122 will continue to monitor the individuals (step 414), until the tracking session terminates by virtue of a predetermined condition, e.g. notification of group arriving at their target destination, pre-defined time has elapsed in combination with no alarm conditions being reported or determined, and/or any other suitable predetermined conditions for terminating the tracking session without compromising the safety of the tracked group.

If monitoring center 122 in step 406 determines that an individual has strayed beyond the pre-defined geo-fencing limitations for the group, an alarm will be triggered (step 408) at monitoring center 122, wherein the monitoring personnel may require confirmation with the group leader, that the individual's location is known or that it is a false alarm. Accordingly, monitoring center 122 or the portable monitoring unit 206 may transmit a message (step 410) via SMS text through a GSM communications network 208, and/or an encrypted alarm signal (step 412) over the satellite network system 118 notifying the group leader of the potentially alarming condition, i.e. missing individual.

The wireless tracking device's 104 communication means 114 receives the SMS text, e.g. ("JOHN IS 50 YARDS AWAY AND MAY BE MISSING, CONFIRM IF THIS IS A FALSE ALARM") and/or encrypted signal where microcontroller's 136 decrypting means 137 (not shown) decrypts the signal for display in text and/or visual format on a group leader's wireless navigational unit 210. Each wireless tracking device 104, 106, 108, 110, 111, 112 acts as nodes and/or routers where their communications means 114 facilitate the group leader's wireless navigational unit 210 receipt of the transmitted SMS text. The wireless navigational unit 210 may comprise of a cell phone, portable display unit or other like communications devices e.g. PDA, Blackberry®, that are well known and used in the art for receiving and/or displaying wireless communications.

Upon receipt of the encrypted alarm signal, wireless tracking device's 104 microcontroller 136 activates the alarm notification means 130 (not shown), causing for example, the sounding of an audio alarm or flashing a light, thereby alerting the group leader of the received encrypted alarm signal 208. In this manner, if the group leader lacks wireless access to a GSM network system 222 and is unable to receive the SMS text, the group leader is visually and/or audibly alerted of the potential alarm and can take the necessary remedial steps to confirm the whereabouts of, and secure the group's individuals.

When the group leader receives the alarm, monitoring center 122 may require group leader to transmit a signal and/or message confirming that it's a false alarm as the individual's location was known and/or authorized. As such, monitoring center 122 may receive confirmation (step 414) of false alarm and may also set new geo-fencing limitations (step 416) to incorporate the individual's authorized presence away from the group's center of gravity. Thereafter, monitoring center 122 may continue tracking (step 418) the group until the tracking session terminates.

Figure 5:
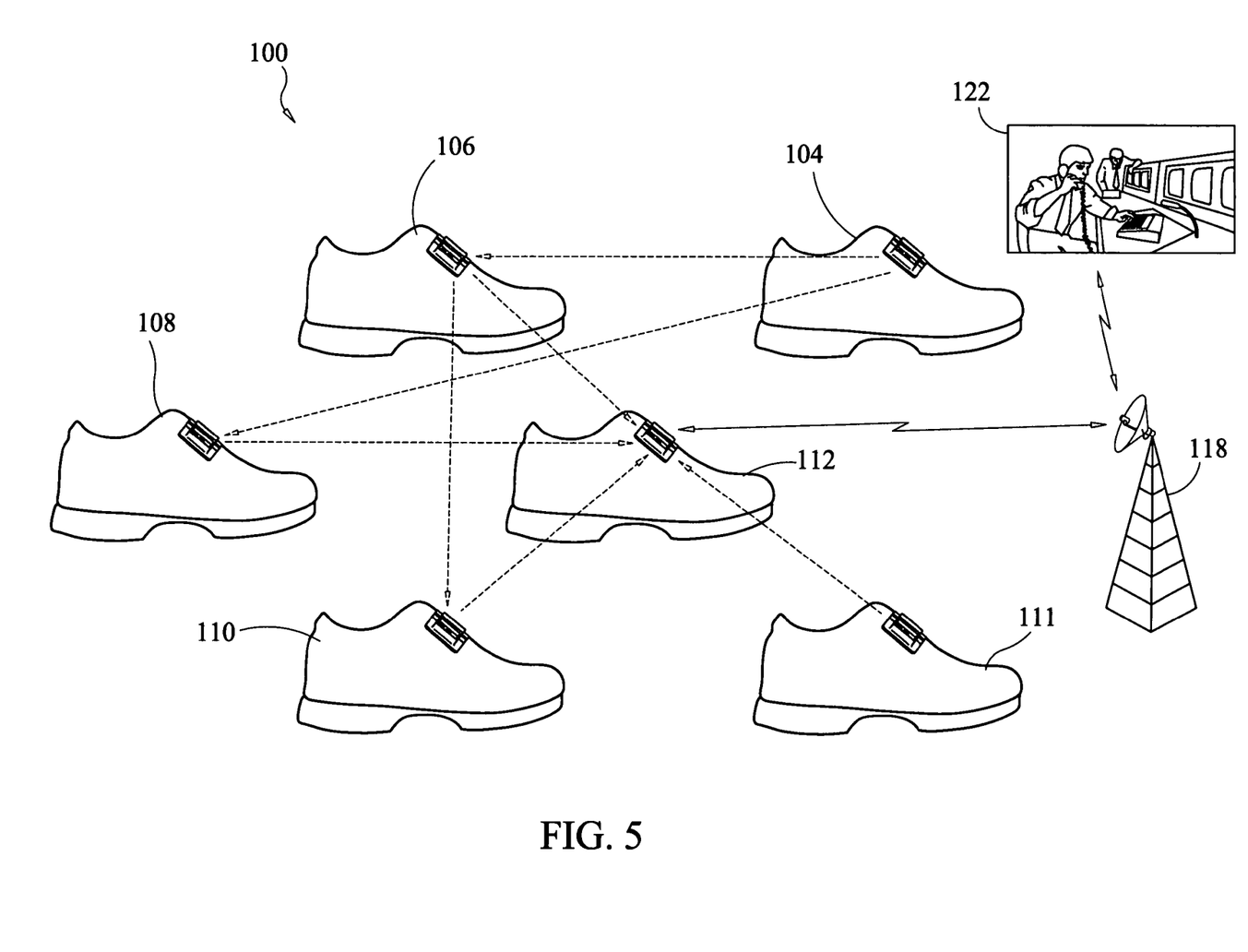
FIG. 5 illustrates a system of tracking a plurality of wireless tracking devices in accordance with an embodiment of the invention.
Figure 6:
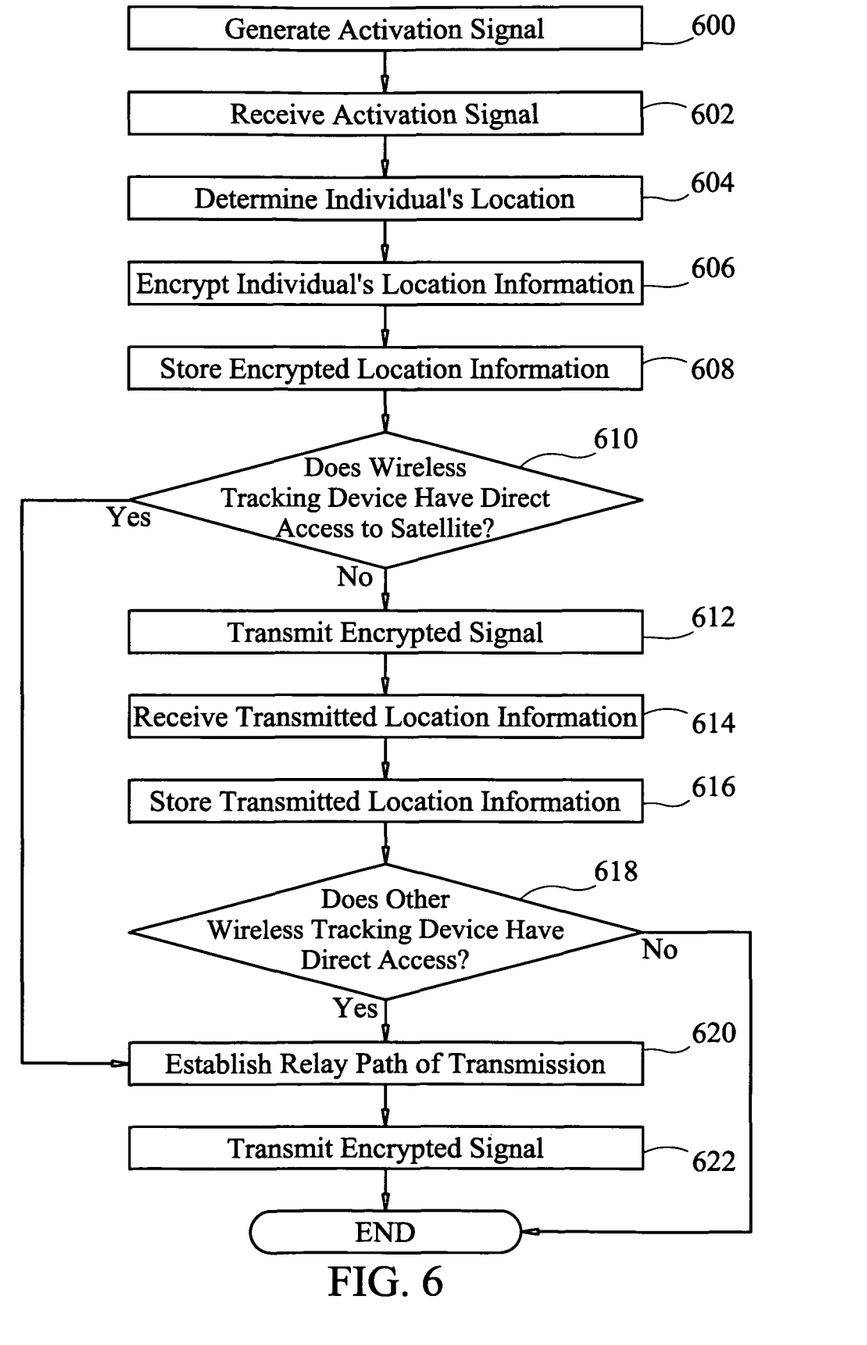
FIG. 6 is an illustrative view of a method of an embodiment of the present invention.

Referring to FIGS. 5 & 6, a system 100 of tracking a plurality of wireless tracking devices 104, 106, 108, 110, 111, 112 in accordance with an embodiment of the invention and an illustrative view of a method of an exemplary embodiment of the present invention are shown. A group leader's wireless tracking device 104 may be configured to activate at least one or more, and/or all of the wireless tracking devices 106, 108, 110, 111, 112 for the individuals within his/her group. Upon activation, the group leader's wireless tracking device's 104 microcontroller 136 causes an activation signal to be generated (step 600) and each wireless tracking device 106, 108, 110, 111, 112 receives the activation signal (step 602), and follows steps 604-608 similar to steps 304-308 as shown in FIG. 3.

Additionally, microcontroller's 136 determining means 200 (not shown) searches for signals of GPS satellite constellation 204 (not shown), to verify whether wireless tracking device 104 has direct access to a satellite network system 118 (step 610). If wireless tracking device 104 has direct access, microcontroller 136 establishes a relay path of transmission in step 620 and transmits the encrypted signal (step 622) containing the individual's location information directly to the wireless communications network system 116 (not shown), which re-transmits the encrypted signal to either monitoring center 122 and/or the portable monitoring unit 206.

However, not all wireless tracking devices 104, 106, 108, 110, 111 within the group may have direct access to a satellite network system 118. As such, a wireless tracking device 104 may randomly query one or more neighboring wireless tracking devices in a manner similar to mesh network systems, to determine whether a wireless tracking device has direct access to a satellite network system 118. It is understood that this mesh network is dynamically formed on an ad-hoc basis as a wireless tracking device 104 systematically queries other neighboring wireless tracking devices 106, 108, 110, 111, 112 for the most direct route to the satellite network system 118 until a wireless tracking device 112 with direct access to a satellite network system 118 is located.

If microcontroller 136 determines that the wireless tracking device in step 610 does not have direct access to a satellite network system 118, the encrypted signal containing individual's location information is transmitted (step 612) to each neighboring wireless tracking device 106, 108, 110, 111, 112 that is queried for direct access, where wireless tracking device's 104 location information is received (step 614) and stored thereon (step 616). However, the first neighboring wireless tracking device 106 queried may also lack direct access. Microcontroller 136 will therefore query other wireless tracking devices 108, 110, 112 to determine if any other wireless tracking devices 108 have direct access (step 618). If direct access cannot be found, microcontroller 136 will cease its query and retain the location information for future transmission.

As microcontroller 136 queries neighboring wireless tracking devices, it is also dynamically establishing a relay path of transmission (step 620) for the most efficient path of transmission of the individual's location information to monitoring center 122. Therefore, if the first neighboring wireless tracking device queried lacks direct access, a second and then a third, etc. will be queried for direct access in step 622.

Once the relay path of transmission has been established and a wireless tracking device 112 with direct access to a satellite network system 118 is found, communication means 114 of that wireless tracking device 112 will thereby transmit an encrypted signal in step 622 containing the location information for each wireless tracking device 104, 106, 108, 110 that was transmitted and received. Each wireless tracking device 106, 108, 110 within the group that lack direct access to the satellite network system 118 will similarly transmit its location information for each individual wearing the footwear 102 along the same dynamically created relay path for transmission to monitoring center 122 via the wireless communications network systems 116.

Wireless tracking device 104 communicates with the communications network systems 116 via its short range protocol or wireless local area network (WLAN). In this manner, each individual's location information is transmitted and stored with a neighboring wireless tracking device 104 for later transmission as needed. Thus, the location information being transmitted to the monitoring center 122 may therefore include any one or more of the following: the absolute geographical location for one, or a plurality of individuals wearing the wireless tracking device in the tracked group. Monitoring center 122 is thus able to monitor signals received from each wireless tracking device 104, 106, 108, 110, 111, 112 and able to locate the group and/or its individuals at any given point in time during a tracking session.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the system and method describe above and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A system for tracking a group of individuals comprising:
   (a) a portable monitoring unit, provided to at least one individual within a tracked group, configured for tracking at least one other individual, within the tracked group, equipped with a wireless tracking device that includes an activation button, which may be selectively depressed to activate and/or deactivate transmission of the individual's location information to the portable monitoring unit and a monitoring center, and wherein said wireless tracking device is also configured for activating at least one other wireless tracking device within the tracked group being monitored, and configured for bi-directional communications with the portable monitoring unit and the monitoring center, and wherein said wireless tracking device is adapted to determine and store absolute location information of said individual with said wireless tracking device and the location information of at least one other individual within said tracked group;
   (b) a geo fence established by the monitoring center, the geo fence having geo-fencing limitations for the at least one individual and the tracked group in real-time based on the tracked group's center of gravity relative to the portable monitoring unit as they travel where the geo fence is in constant motion and the geo fence is defined by first determining location of a majority of the tracked group's members and then setting a maximum allowed distance between each member of the tracked group and the majority of the tracked group's members, and wherein the monitoring center sets new geo-fencing limitations to incorporate an authorized presence of a member of the tracked group who has moved away from the tracked group's center of gravity;
   (c) means for receiving an activation signal from a communications means of another wireless tracking device within said tracked group and means for determining said wireless tracking device's direct access to a satellite network system;
   (d) means for dynamically creating a relay path of transmission to said satellite network system by querying nearby wireless tracking devices within the tracked group until at least one wireless tracking device with direct access to said satellite network system is determined; and
   (e) means for transmitting an encrypted signal using a short range wireless protocol that contains location information of at least one individual within said tracked group along said dynamically created relay path of transmission, where said individual's location information is received and stored for transmission along the dynamically created relay path via said satellite network system.

2. The system of claim 1, wherein said means for receiving an activation signal is further configured for receiving at least one encrypted alarm signal from a monitoring center.

3. The system of claim 1, wherein said short range wireless protocol includes any one or more of the following: WiHLoN™, Bluetooth®, ZigBee, 802.11 series.

4. The system of claim 1, wherein said wireless tracking device has a unique identifier for identifying said individual with monitoring center.

5. The system of claim 1, wherein said satellite network system may include one of the following: a geosynchronous or low earth orbit satellite.

6. The system of claim 1, wherein said location information may comprise of: said individual's absolute geographical location, the date and time said location information was determined or said individual's location relative to other individuals within the tracked group.

7. The system of claim 1, wherein said location information being transmitted to monitoring center or the portable monitoring unit may therefore include anyone or more of the following: the absolute geographical location for one, some or all individuals wearing the wireless tracking device in the tracked group.

8. A method for tracking a group of individuals comprising:
   (a) providing at least one individual within a tracked group with a portable monitoring unit, configured for tracking at least one other individual within the tracked group, equipped with a wireless tracking device that includes an activation button, which may be selectively depressed to activate and/or deactivate transmission of the individual's location information to the portable monitoring unit and a monitoring center, and wherein said wireless tracking device is also configured for activating at least one other wireless tracking device within the tracked group being monitored, and configured for bi-directional communications with the portable monitoring unit and the monitoring center, and wherein said wireless tracking device is adapted to determine and store absolute location information of said individual wearing said wireless tracking device and the location information of at least one other individual within said tracked group;
   (b) determining location of a majority of the tracked group's members;
   (c) establishing a geo fence by the monitoring center, the geo fence having geo-fencing limitations for the at least one individual and the tracked group in real-time based on the tracked group's center of gravity relative to the portable monitoring unit as they travel where the geo fence is in constant motion and the geo fence is defined as the maximum allowed distance between each member of the tracked group and the majority of the tracked group's members, and setting new geo-fencing limitations to incorporate an authorized presence of a member of the tracked group who has moved away from the tracked group's center of gravity;

(d) receiving an activation signal from a communications means of another wireless tracking device within said tracked group and determining said wireless tracking device's direct access to a satellite network system;

(e) dynamically creating a relay path of transmission to said satellite network system by querying nearby wireless tracking devices within the tracked group until at least one wireless tracking device with direct access to said satellite network system is determined; and (f) transmitting an encrypted signal using a short range wireless protocol that contains location information of at least one individual within said tracked group along said dynamically created relay path of transmission, where said individual's location information is received and stored for transmission along the dynamically created relay path via said satellite network system.

9. The method of claim 8, wherein further comprising receiving at least one encrypted alarm signal from a monitoring center.

10. The method of claim 8, wherein said short range wireless protocol includes any one or more of the following: WiHLoN™, Bluetooth®, ZigBee, 802.11 series.

11. The method of claim 8, wherein said tracking device has a unique identifier for identifying said individual with monitoring center.

12. The method of claim 8, wherein said satellite network system may include one of the following: a geosynchronous or low earth orbit satellite.

13. The method of claim 8, wherein said location information may comprise of but is not limited to: said individual's absolute geographical location, the date and time said location information was determined, said individual's location relative to other individuals within the tracked group.

14. The method of claim 8, wherein said location information being transmitted to monitoring center or the portable monitoring unit may therefore include anyone or more of the following but is not limited to: the absolute geographical location for one, some or all individuals wearing the wireless tracking device in the tracked group.

15. The system of claim 1, wherein the monitoring center sets the new geo-fencing limitations upon receipt of a false alarm from the tracked group's leader regarding the member's authorized presence away from the tracked group's center of gravity.

16. The method of claim 8, wherein the new geo-fencing limitations are set upon receipt of a false alarm from the tracked group's leader regarding the member's authorized presence away from the tracked group's center of gravity.

* * * * *